United States Patent
Ishioka et al.

(10) Patent No.: US 10,052,071 B2
(45) Date of Patent: Aug. 21, 2018

(54) RADIATION IMAGING APPARATUS AND CONTROL METHOD FOR RADIATION IMAGING APPARATUS

(71) Applicant: CANON KABUSHIKI KAISHA, Tokyo (JP)

(72) Inventors: Toshiya Ishioka, Kawasaki (JP); Akehiko Uchiyama, Kawasaki (JP); Hideaki Morita, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/420,231

(22) Filed: Jan. 31, 2017

(65) Prior Publication Data

US 2017/0224290 A1    Aug. 10, 2017

(30) Foreign Application Priority Data

Feb. 9, 2016   (JP) .................. 2016-023079

(51) Int. Cl.
   *A61B 5/00* (2006.01)
   *A61B 6/00* (2006.01)

(52) U.S. Cl.
   CPC .......... *A61B 5/7405* (2013.01); *A61B 6/4233* (2013.01); *A61B 6/46* (2013.01); *A61B 6/5258* (2013.01); *A61B 6/54* (2013.01)

(58) Field of Classification Search
   CPC ........ A61B 5/7405; A61B 6/4233; A61B 6/46
   See application file for complete search history.

(56) References Cited

U.S. PATENT DOCUMENTS

| | | | |
|---|---|---|---|
| 8,952,332 B2 | 2/2015 | Uchiyama | H04N 5/32 |
| 9,551,794 B2 | 1/2017 | Uchiyama | G01T 1/17 |
| 2004/0258204 A1 | 12/2004 | Nokita et al. | 378/91 |
| 2005/0141048 A1* | 6/2005 | Mizutani | G06K 9/0002 358/474 |
| 2010/0054399 A1* | 3/2010 | Nishino | A61B 6/4233 378/28 |
| 2013/0279661 A1 | 10/2013 | Tamura et al. | 378/98 |
| 2015/0085980 A1* | 3/2015 | Kitano | H01L 27/14663 378/62 |

(Continued)

FOREIGN PATENT DOCUMENTS

| | | |
|---|---|---|
| EP | 1492333 | 12/2004 |
| EP | 2977010 | 1/2016 |
| JP | 2005-013272 | 1/2005 |

OTHER PUBLICATIONS

European Extended Search Report dated Aug. 14, 2017 in counterpart application EP 17153463.9.

*Primary Examiner* — Hugh H Maupin
(74) *Attorney, Agent, or Firm* — Fitzpatrick Cella Harper and Scinto

(57) ABSTRACT

An X-ray imaging apparatus including a sensor unit with a sensor array configured to generate a signal corresponding to X-rays and a sound-production unit configured to make a notification by sound production causes the sound-production unit to execute sound production in response to detection of an event. If an event including a sound-production request occurs during a period including a period of reading out a signal from the sensor array, the X-ray imaging apparatus restricts execution of sound production by the sound-production unit.

18 Claims, 11 Drawing Sheets

(56) References Cited

U.S. PATENT DOCUMENTS

2016/0061970 A1    3/2016   Asai et al. .............. G01T 7/005
2016/0358458 A1*   12/2016   Kudo ................... G08B 29/185
2017/0031035 A1    2/2017   Ishioka ................... G01T 1/208

* cited by examiner

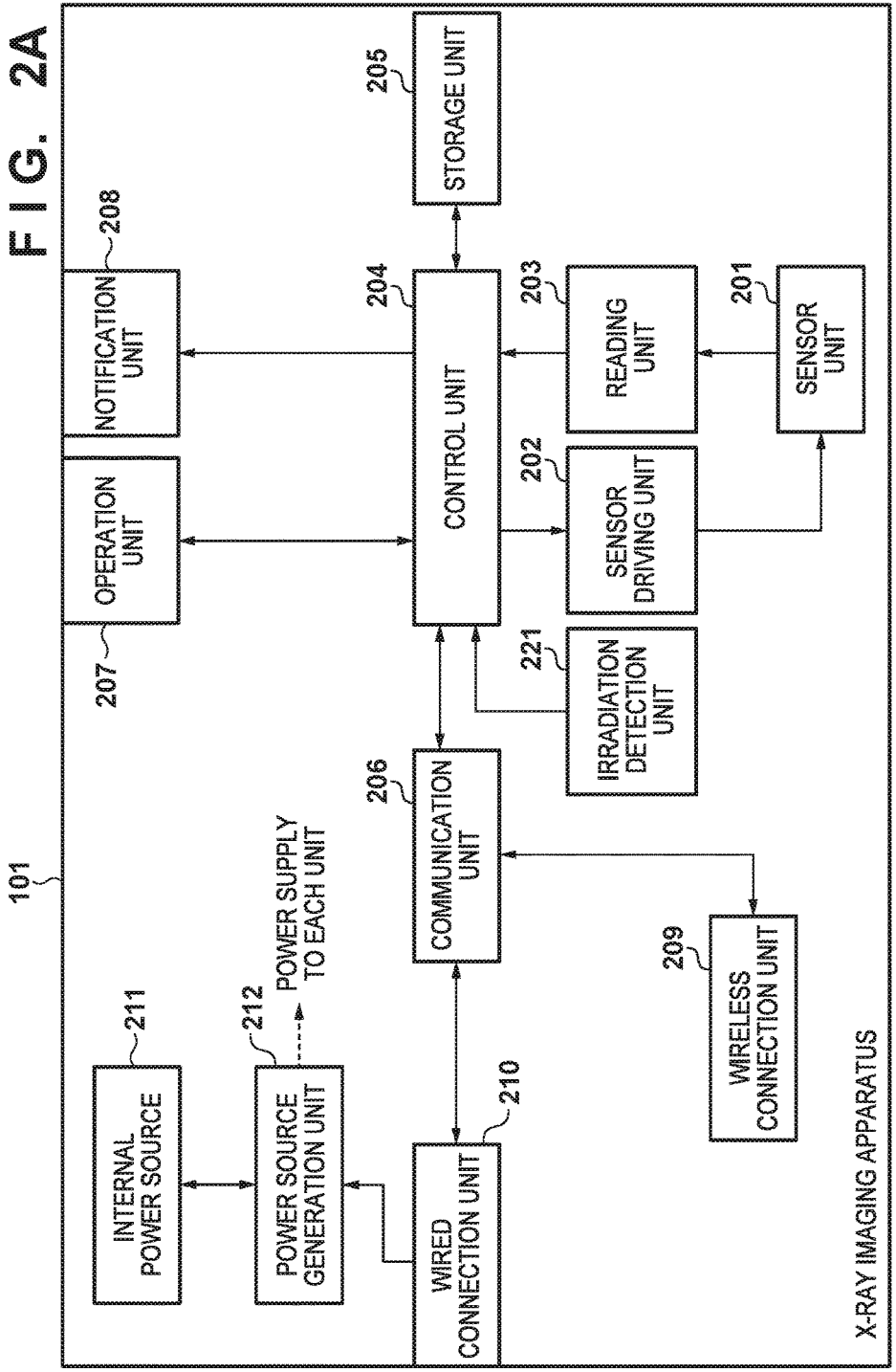

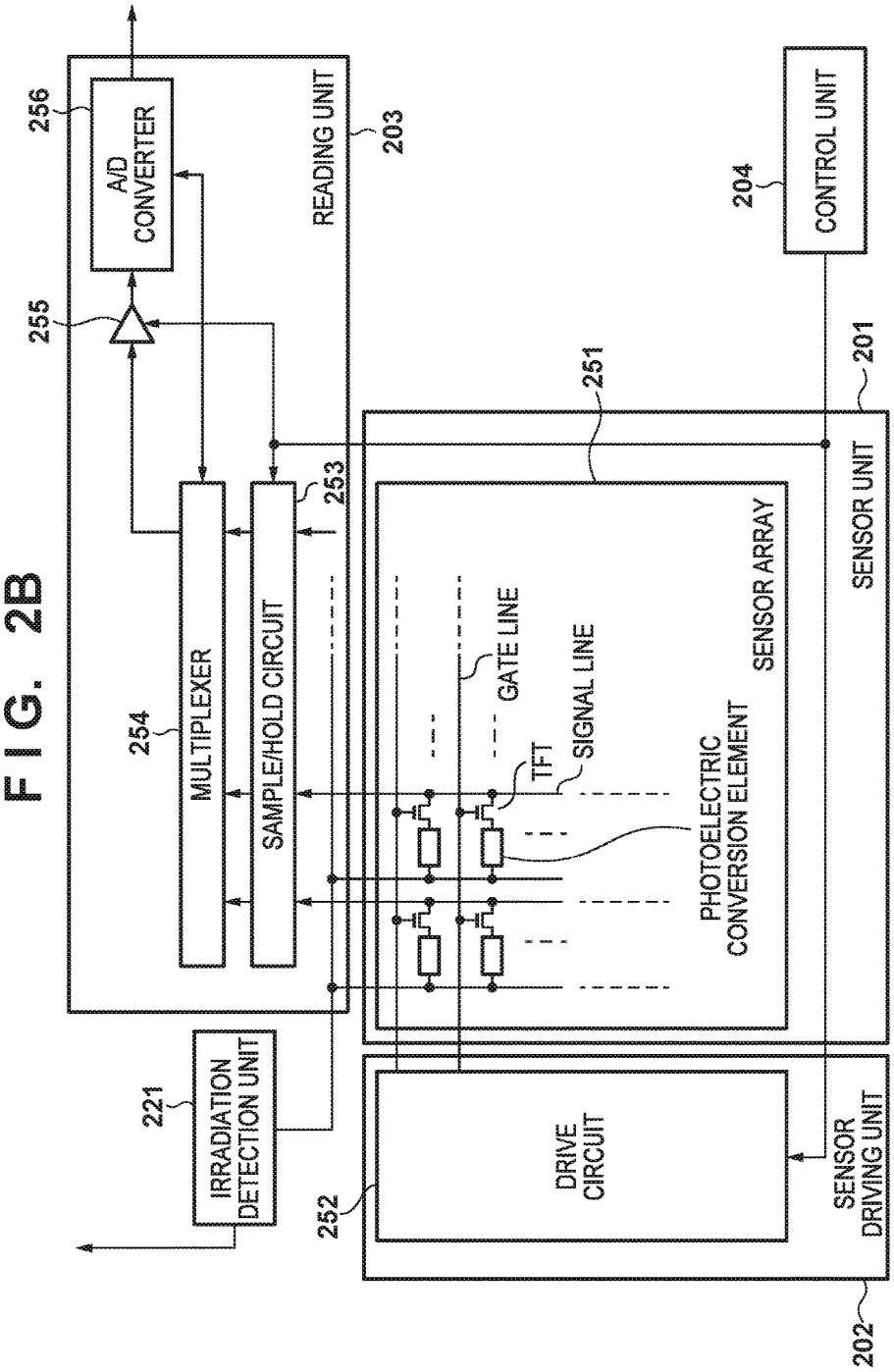

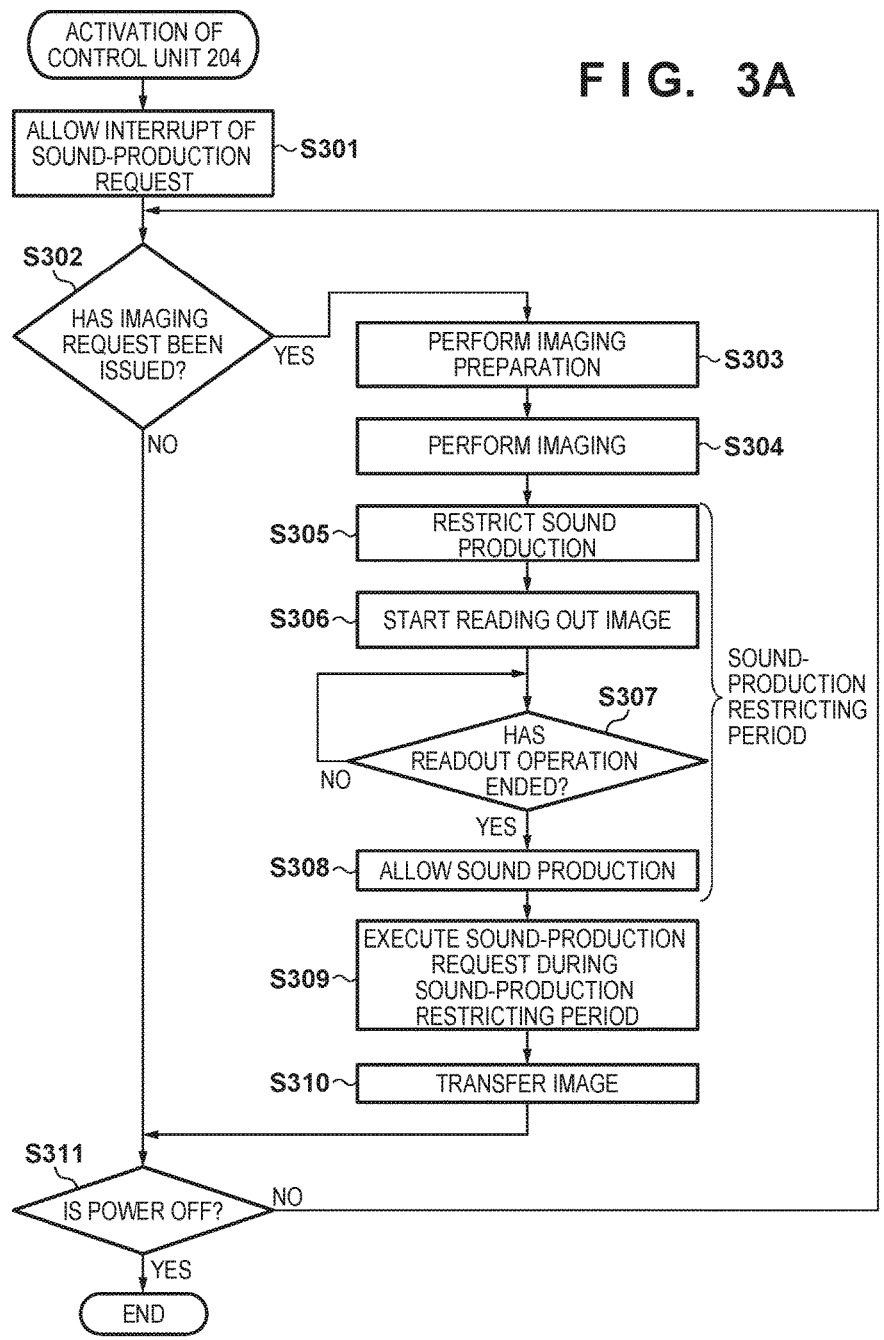

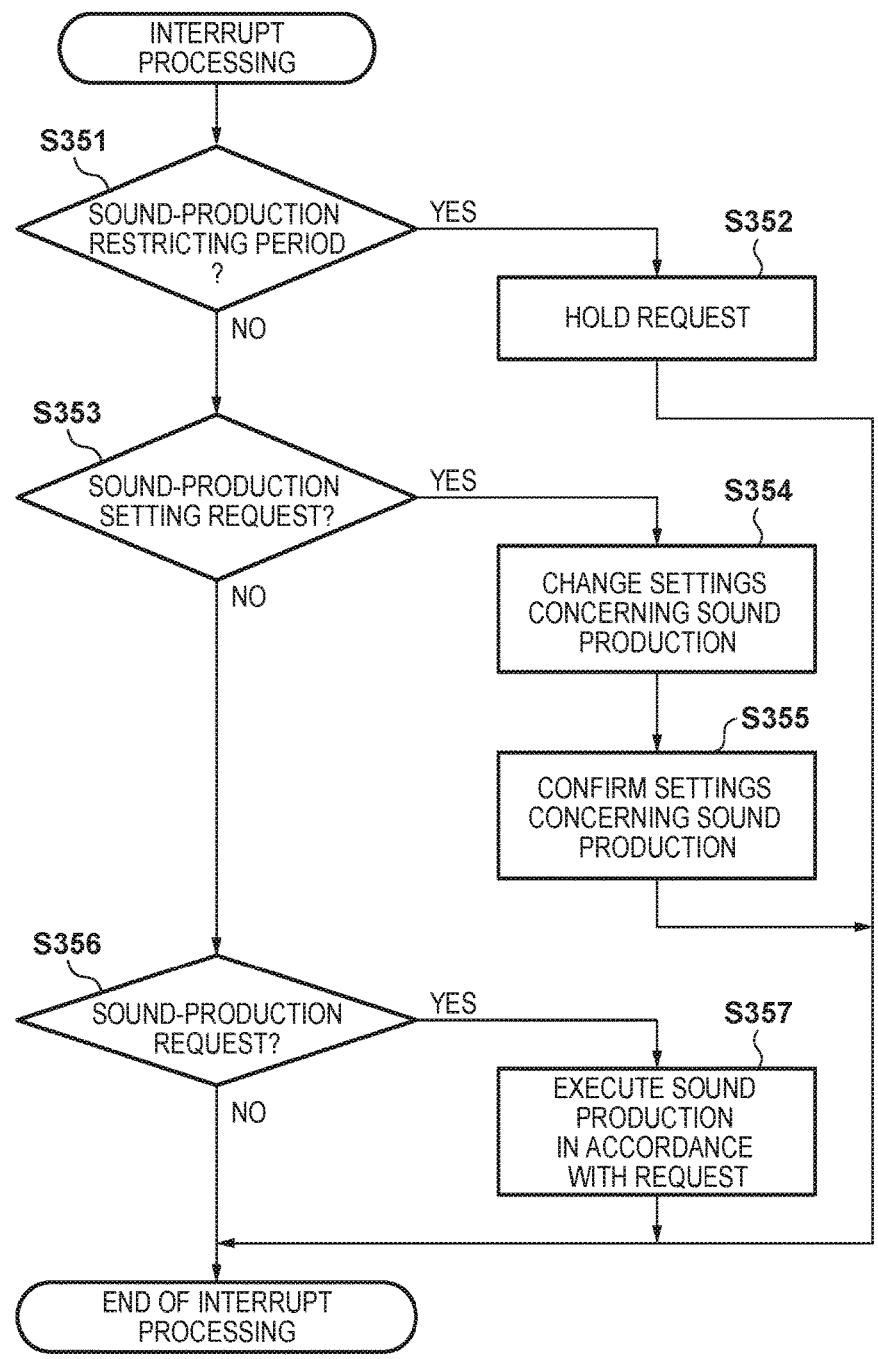

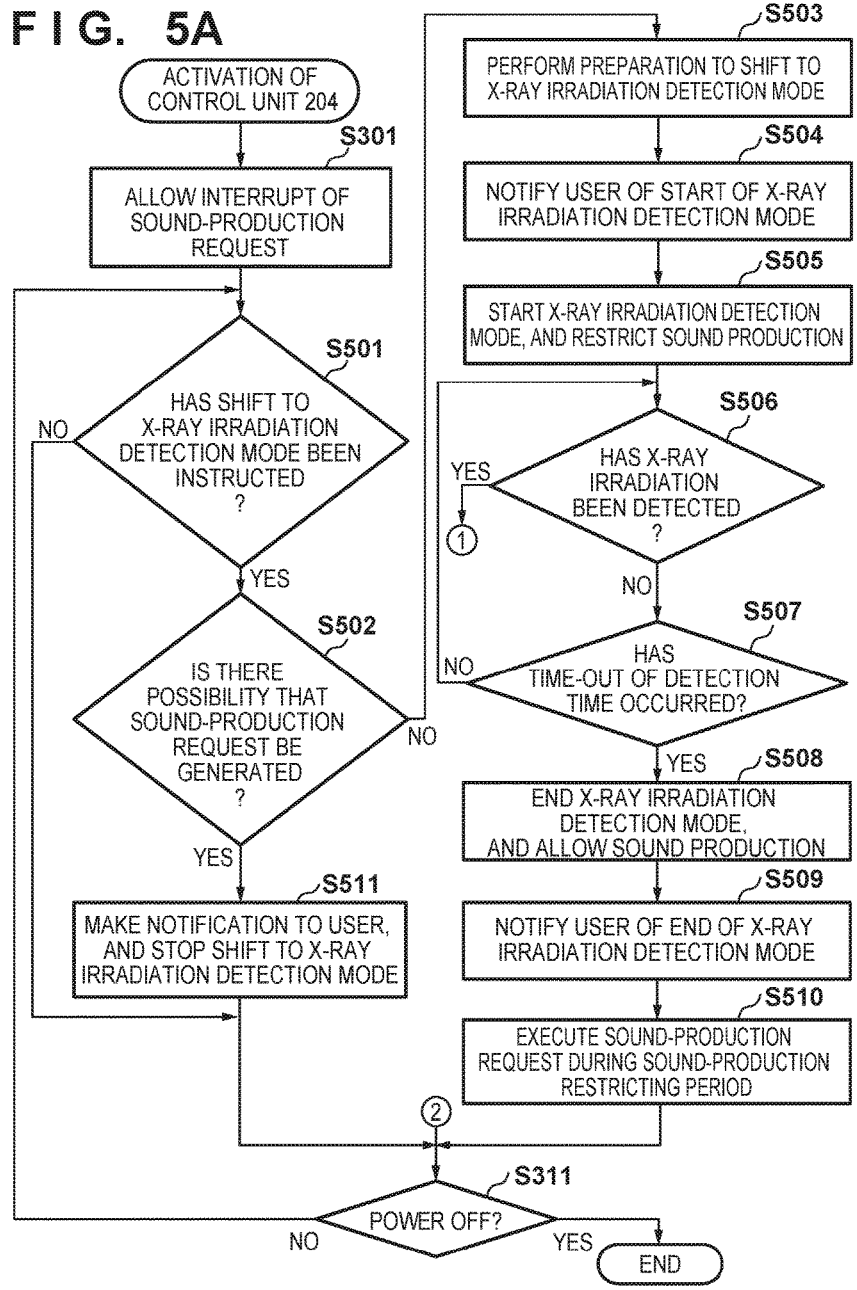

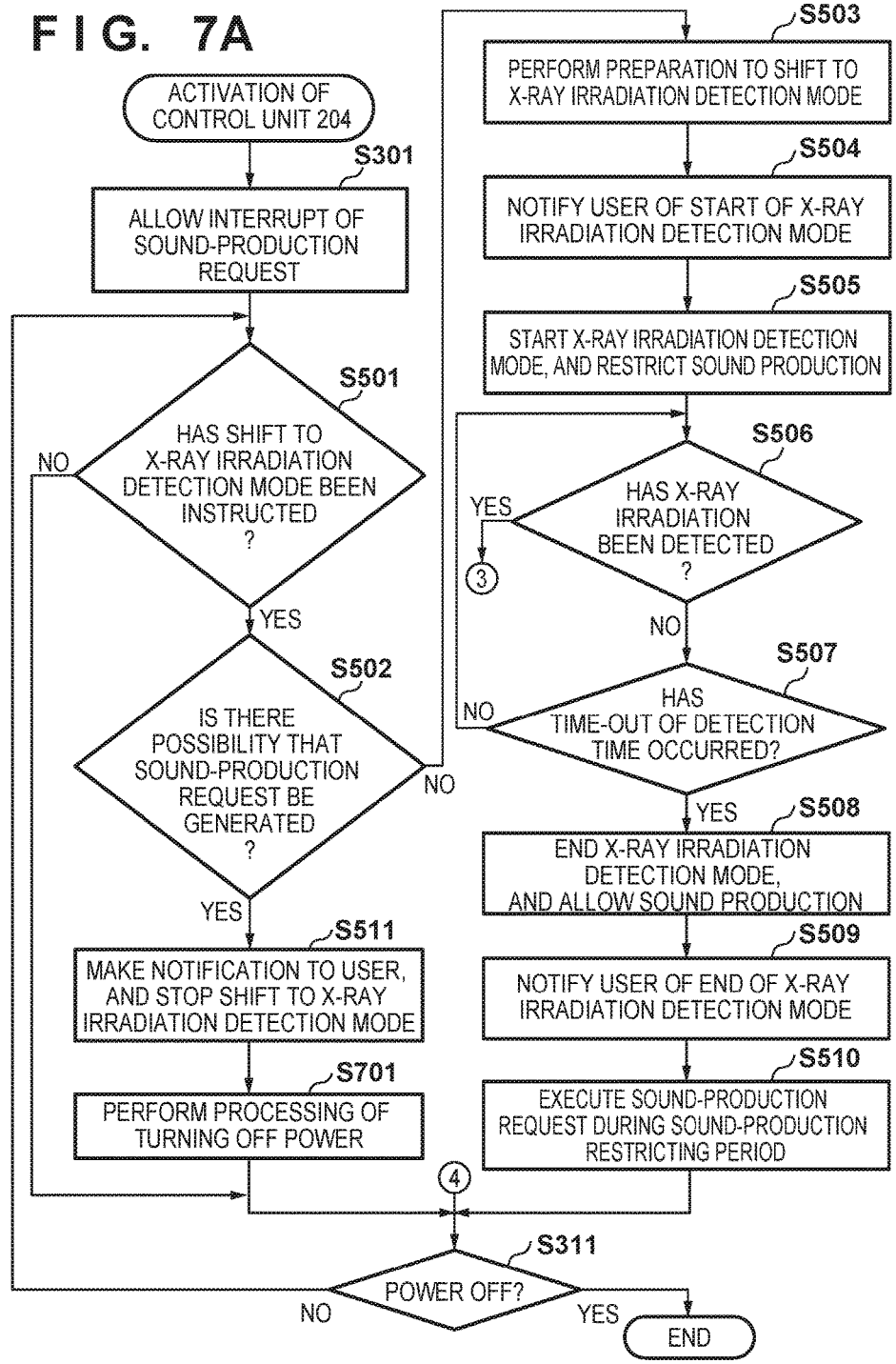

RADIATION IMAGING APPARATUS AND CONTROL METHOD FOR RADIATION IMAGING APPARATUS

BACKGROUND OF THE INVENTION

Field of the Invention

The present invention relates to a radiation imaging apparatus and a control method for the radiation imaging apparatus.

Description of the Related Art

In general, an X-ray imaging apparatus which irradiates an object with X-rays generated by an X-ray source, detects the intensity distribution of X-rays transmitted through the object, and converts it into an image or an X-ray imaging system including the apparatus has become commercially available. In recent years, an X-ray imaging apparatus which converts X-rays into visible light by a phosphor, converts the visible light into an electrical signal by a photosensor, and outputs an X-ray image as digital data without using an X-ray film has become widespread.

Such X-ray imaging apparatus may be provided with a notification function for notifying the user of the operation state of itself. A practical example of the notification function is a function using light or a sound. Japanese Patent Laid-Open No. 2005-013272 proposes an X-ray imaging apparatus which implements a notification function by mounting or connecting a light emitting component such as an LED or lamp or a sound-production component such as a loudspeaker. The notification function allows the user to recognize information about the state or operation of the X-ray imaging apparatus, for example, whether the X-ray imaging apparatus is active, or the X-ray imaging apparatus is in an X-ray imaging enable state.

In general, a component driven by electricity generates electromagnetism during driving. Since a sound-production component like a loudspeaker includes a component such as a coil which is intended to generate electromagnetism, the intensity of generated electromagnetism is higher than that of other components. On the other hand, the X-ray imaging apparatus is provided with a detection mechanism or sensor with high sensitivity, such as a photoelectric conversion sensor array or a mechanism for X-ray detection. Therefore, in the case of the X-ray imaging apparatus, an electromagnetic influence, exerted by driving the sound-production component, on the detection mechanism or sensor may cause inconvenience to X-ray imaging. Especially, in the case of a cassette-type portable X-ray imaging apparatus, since various components are arranged in a limited space, it is difficult to ensure the distance between components such as the sound-production component and the sensor array, and the sound-production component tends to influence X-ray imaging.

SUMMARY OF THE INVENTION

According to an embodiment of the present invention, the influence of a sound-production component on X-ray imaging is reduced.

According to one aspect of the present invention, there is provided a radiation imaging apparatus comprising: a sensor unit including a sensor array configured to generate a signal corresponding to radiation; a sound-production unit configured to make a notification by sound production; and a notification unit configured to cause the sound-production unit to execute sound production in response to detection of an event, wherein if an event including a sound-production request occurs during a first period including a period of reading out a signal from the sensor array, execution of sound production by the sound-production unit is restricted.

According to another aspect of the present invention, there is provided a control method for a radiation imaging apparatus including a sensor unit with a sensor array configured to generate a signal corresponding to radiation and a sound-production unit configured to make a notification by sound production, the method comprising: causing the sound-production unit to execute sound production in response to detection of an event; and restricting, if an event including a sound-production request occurs during a first period including a period of reading out a signal from the sensor array, execution of sound production by the sound-production unit.

Further features of the present invention will become apparent from the following description of exemplary embodiments (with reference to the attached drawings).

BRIEF DESCRIPTION OF THE DRAWINGS

FIG. 2A is a block diagram showing an example of the arrangement of an X-ray imaging apparatus according to the first embodiment;

FIG. 2B is a circuit diagram showing an example of the detailed arrangement of a sensor unit;

FIG. 3A is a flowchart illustrating X-ray imaging processing at the time of a synchronization mode;

FIG. 3B is a flowchart for explaining interrupt processing;

FIGS. 5A and 5B are flowcharts illustrating X-ray imaging processing at the time of an X-ray irradiation detection mode;

FIGS. 7A and 7B are flowcharts illustrating X-ray imaging processing at the time of the console-less mode.

DESCRIPTION OF THE EMBODIMENTS

Some preferred embodiments of the present invention will be described below with reference to the accompanying drawings.

First Embodiment

Figure 1:
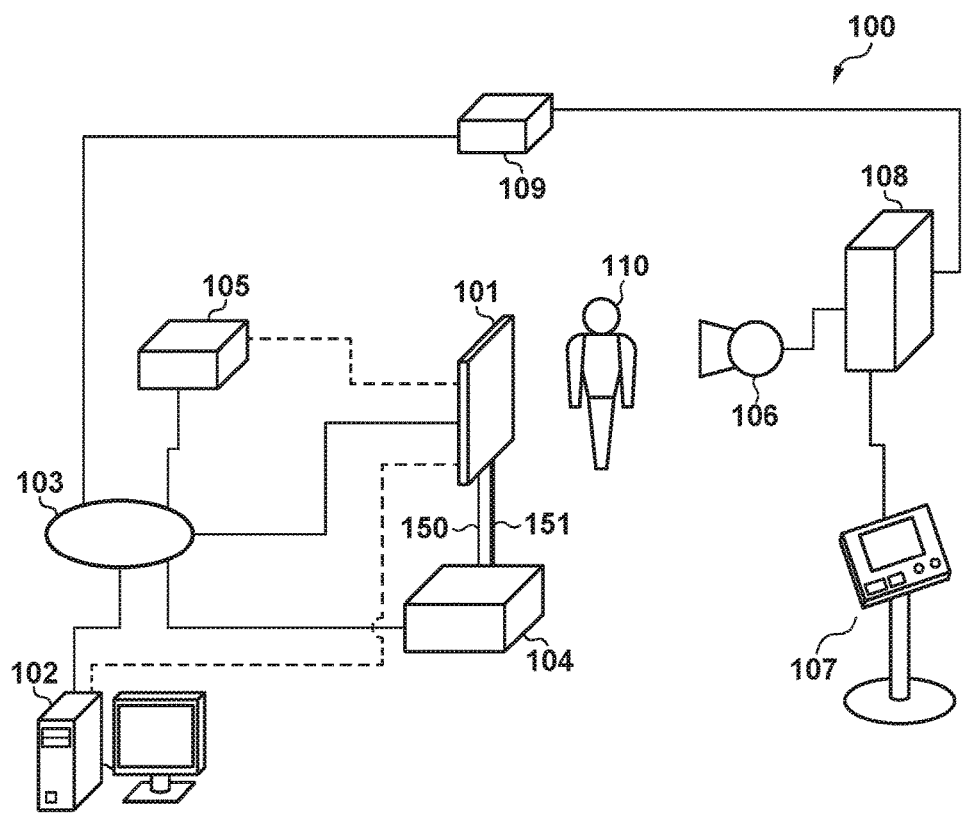
FIG. 1 is a view showing an example of the arrangement of an X-ray imaging system according to embodiments.

Embodiments will be described below using an X-ray imaging apparatus as a radiation imaging apparatus. The first embodiment shows an example in which an X-ray imaging apparatus operates in a synchronization mode of capturing an image in synchronism with an X-ray generating apparatus and an image readout period is set as a period during which the output of a sound from a sound-production unit provided in the X-ray imaging apparatus is restricted. FIG. 1 shows an example of the arrangement of an X-ray imaging system 100 according to the first embodiment. The arrangement of the X-ray imaging system 100 according to the first embodiment will be described with reference to FIG. 1.

An X-ray imaging apparatus 101 has one or both of a wired communication function and a wireless communication function, and can exchange data with an imaging console 102 via a communication path. The imaging console 102 is constructed by, for example, a computer apparatus (a PC or the like) having a display function such as a monitor and a function of accepting an input instruction from the user (radiographer or operator). The imaging console 102 can send, to the X-ray imaging apparatus 101, an instruction from the user, or receive an image acquired by the X-ray imaging apparatus 101 and present it to the user. Furthermore, the imaging console 102 has one or both of a wired communication function and a wireless communication function. Note that FIG. 1 shows an example in which the imaging console 102 is of a standalone type. However, no such restriction is imposed on an actual operation, and a note PC, tablet device, or the like of a portable type may be used as the imaging console 102.

The X-ray imaging apparatus 101 sends an acquired X-ray image to the imaging console 102. The X-ray image may be sent from the X-ray imaging apparatus 101 to the imaging console 102 via a LAN 103 or may be directly sent from the X-ray imaging apparatus 101 to the imaging console 102. For example, the LAN 103 is formed by a wired cable, and is connected to the X-ray imaging apparatus 101 and the imaging console 102, thereby allowing exchange of data such as an X-ray image.

Furthermore, the X-ray imaging apparatus 101 may have a power receiving function together with a connection for wired communication. In this case, by connecting, to the X-ray imaging apparatus 101, a power source unit 104 which can implement power supply and communication at the same time, the power source unit 104 can supply power to the X-ray imaging apparatus 101 while mediating communication between the X-ray imaging apparatus 101 and the imaging console 102. Referring to FIG. 1, lines 150 and 151 each connecting the X-ray imaging apparatus 101 and the power source unit 104 indicate a communication wiring and a power supply wiring, respectively. These two wirings may be accommodated in one cable or separately prepared. FIG. 1 shows a state in which the power source unit 104 is connected to the LAN 103. However, the power source unit 104 and the imaging console 102 may be directly connected.

If the X-ray imaging apparatus 101 communicates with the imaging console 102 by wireless communication, it may be connected to the LAN 103 via an access point (AP 105). Note that FIG. 1 shows a state in which the AP 105 is connected to the LAN 103 but the AP 105 and the imaging console 102 may be directly connected. Furthermore, the X-ray imaging apparatus 101 and the imaging console 102 may have a function of directly exchanging data with each other via wireless or wired communication. An example of the communication path when the X-ray imaging apparatus 101 and the imaging console 102 exchange data has been explained.

Referring to FIG. 1, an X-ray generating apparatus 108 is connected to an X-ray tube 106 for generating X-rays, an X-ray generation console 107 for accepting a user operation such as an X-ray generation instruction, and an X-ray apparatus connection device 109 for performing communication connection to the LAN 103. Note that the X-ray generating apparatus 108 and the X-ray imaging apparatus 101 can communicably connected via the X-ray apparatus connection device 109 and the LAN 103. The X-ray imaging apparatus 101 implements the synchronization mode of synchronizing an imaging operation and an X-ray irradiation operation by the X-ray generating apparatus 108 by communication via the connection.

The procedure of X-ray imaging of an object 110 by the X-ray imaging system 100 will now be described. To perform X-ray imaging of the object 110, the user arranges the X-ray imaging apparatus 101 at a position where it is irradiated with X-rays emitted by the X-ray tube 106 and transmitted through the object 110. Next, the user activates the X-ray imaging apparatus 101, and then operates the imaging console 102 to set the X-ray imaging apparatus 101 in an imaging enable state. Subsequently, the user operates the X-ray generation console 107 to set X-ray irradiation conditions. After the end of the above-described operation, the user confirms that imaging preparation including the object 110 is completed, and presses an exposure switch provided on the X-ray generation console 107, thereby instructing the X-ray generating apparatus 108 to perform X-ray exposure.

Upon accepting the X-ray exposure instruction, the X-ray generating apparatus 108 notifies, via the X-ray apparatus connection device 109 and the LAN 103, the X-ray imaging apparatus 101 of a signal indicating that X-ray irradiation starts. Note that in FIG. 1, the X-ray imaging apparatus 101 and the X-ray generating apparatus 108 are connected via the X-ray apparatus connection device 109 and the LAN 103. However, the connection form is not limited to this. For example, the X-ray generating apparatus 108 and the X-ray imaging apparatus 101 may be directly connected without intervention of the X-ray apparatus connection device 109 and the LAN 103. If the X-ray imaging apparatus 101 has a function of detecting X-ray irradiation, the X-ray generating apparatus 108 need not notify the X-ray imaging apparatus 101 of irradiation, as will be described later in the second embodiment.

Upon receiving, from the X-ray generating apparatus 108, the signal indicating that X-ray irradiation starts, the X-ray imaging apparatus 101 confirms whether it is ready for X-ray irradiation. If there is no problem, the X-ray imaging apparatus 101 returns irradiation allowance to the X-ray generating apparatus 108. Upon receiving the irradiation allowance from the X-ray imaging apparatus 101, the X-ray generating apparatus 108 drives the X-ray tube 106 to perform X-ray irradiation. Upon detecting the end of X-ray irradiation, the X-ray imaging apparatus 101 starts generating an X-ray image, and sends the generated X-ray image to the imaging console 102 via the above-described communication path. The end of X-ray irradiation can be detected by various methods, for example, a notification from the X-ray generating apparatus 108 or detection of a lapse of a predetermined irradiation time. The imaging console 102 stores the data (X-ray image data) received from the X-ray imaging apparatus 101 or displays it on a display unit.

The arrangement of the X-ray imaging apparatus 101 will be described next with reference to FIG. 2A. The X-ray imaging apparatus 101 includes a sensor unit 201 and a notification unit 208. In the X-ray imaging apparatus 101, the sensor unit 201 including a sensor array for generating a signal corresponding to X-rays and the notification unit 208 including a sound-production unit for making a notification by sound reproduction are accommodated in a housing. Note that the sound-production unit may be connectable to the housing. The sensor unit 201 of the X-ray imaging apparatus 101 converts incident X-rays into an electrical signal. The sensor unit 201 is formed by a scintillator (not shown) and a photodetector array (to be referred to as a sensor array 251 (FIG. 2B) hereinafter). The scintillator and the sensor array 251 have two-dimensional planar shapes and are adjacent to each other so that the planes face each other. The scintillator is excited by radiation such as X-rays and generates visible light. Charges corresponding to the period and the intensity of the visible light are accumulated in the respective pixels of the sensor array 251. Note that the arrangement of the sensor unit 201 is not limited to this, and a direct conversion type sensor for directly converting X-rays into an electrical signal may be used.

FIG. 2B is a circuit diagram showing an example of the detailed arrangement of the sensor unit 201, a sensor driving unit 202, and a reading unit 203. The sensor unit 201 includes the scintillator (not shown) and the sensor array 251 in which the pixels are two-dimensionally arrayed. The sensor driving unit 202 includes a drive circuit 252. A plurality of pixels on a row in the sensor array 251 are connected to one gate line, and simultaneously addressed by the drive circuit 252. The reading unit 203 includes a sample/hold circuit 253, a multiplexer 254, an amplifier 255, and an A/D converter 256. The sample/hold circuit 253 reads out charges (signals) accumulated in the pixels addressed by the drive circuit 252 and holds them. The charges (signals) of the respective pixels held in the sample/hold circuit 253 are sequentially output to the amplifier 255 via the multiplexer 254. The signals of the pixels read out by the sensor array 251 are amplified by the amplifier 255, and then converted into digital values by the A/D converter 256. When scanning of one row on the sensor array 251 ends, the drive circuit 252 drives the next row on the sensor array 251, thereby performing sequential scanning. When scanning of all the rows ends, the digital values of the signals read out from all the pixels of the sensor array 251 are obtained. The obtained digital values form an X-ray image. Note that an irradiation detection unit 221 shown in FIGS. 2A and 2B is a component used in the second embodiment and can be omitted in this embodiment. The irradiation detection unit 221 will be described in the second embodiment.

A control unit 204 drives the drive circuit 252 of the sensor driving unit 202, and the sample/hold circuit 253 and multiplexer 254 of the reading unit 203 so as to implement the above-described sequential scanning. This causes the reading unit 203 to read out the signals from the sensor unit 201 in cooperation with the sensor driving unit 202, and converts them into digital information. When extracting charges accumulated in the sensor array 251, the control unit 204 instructs the sensor driving unit 202 to select a specific row or column of the sensor array 251 to extract charges. The reading unit 203 reads out signals from the selected row or column of the sensor array 251, and amplifies them, thereby performing digitalization. The data digitalized by the reading unit 203 is sent to the control unit 204, and stored by the control unit 204 as an X-ray image in a storage unit 205. Using a communication function (communication unit 206), the control unit 204 externally sends the X-ray image stored in the storage unit 205. Note that the externally sent X-ray image is the X-ray image stored in the storage unit 205 or the X-ray image having undergone some processing. In some cases, the X-ray image remains in the storage unit 205 without being externally sent.

Note that as for the arrangement of the sensor unit 201, the type of scintillator, and the types of photodetector, control unit 204, storage unit 205, and the like are not particularly limited, and various arrangements can be used.

The control unit 204 performs processing associated with control of each unit of the X-ray imaging apparatus 101. For example, the control unit 204 outputs, to the sensor driving unit 202, an instruction to drive the sensor unit 201 for imaging, saves, in the storage unit 205, the X-ray image read out by the reading unit 203 from the sensor unit 201, or reads out the X-ray image saved in the storage unit 205. The control unit 204 also sends the X-ray image to another apparatus via the communication unit 206, receives an instruction from an external apparatus via the communication unit 206, or switches activation/stop of the X-ray imaging apparatus 101 in response to an operation from an operation unit 207. The control unit 204 also controls to notify the user of the operation status or error state of the X-ray imaging apparatus 101 by light or a sound using the notification unit 208. Note that the above-described processing contents are processed by one control unit 204 in this embodiment. However, a plurality of control units 204 may be provided to share the processing. As for practical implementation of the control unit 204, a CPU (Central Processing Unit), a MPU (Micro Processing Unit), an FPGA (Field-Programmable Gate Array), a CPLD (Complex Programmable Logic Device), or the like can be used, and the present invention is not particularly limited.

The storage unit 205 is used to save the X-ray image acquired by the X-ray imaging apparatus 101, or log information indicating an internal processing result or the like. If the control unit 204 is a component using software, such as a CPU, the storage unit 205 can store a program for it. Note that practical implementation of the storage unit 205 is not limited, and the storage unit 205 can be implemented by various combinations of semiconductor memories, HDDs, volatile/nonvolatile memories. This embodiment illustrates only one storage unit 205. However, a plurality of storage units 205 can be arranged.

The communication unit 206 performs processing for implementing communication between the X-ray imaging apparatus 101 and another apparatus. The communication unit 206 according to this embodiment is connected to a wireless connection unit 209 for wireless communication, and can communicate with the AP 105 or the imaging console 102 via the wireless connection unit 209. An example of the wireless connection unit 209 is an antenna for wireless communication. The communication unit 206 is connected to a wired connection unit 210, and can communicate with the power source unit 104 or the imaging console 102 via the wired connection unit 210. The wired connection unit 210 has a mechanism capable of receiving power when connected to the power source unit 104. An example of the mechanism is a connector including a communication pin and a power source pin. The wired connection unit 210 having such mechanism implements wired communication and reception of power supply using the power source unit 104. Note that the communication unit 206 is not limited to the above arrangement, and may have an arrangement including only the wired communication function or the wireless communication function. The standard and method of the communication are not particularly limited.

The X-ray imaging apparatus 101 includes an internal power source 211. In this embodiment, the internal power source 211 is a chargeable battery, and is detachable from the main body of the X-ray imaging apparatus 101. The internal power source 211 is not limited to this example, and whether the internal power source 211 is rechargeable or unrechargeable, whether the internal power source 211 is detachable or undetachable, a power generation method, and the like are not limited.

A power source generation unit 212 generates a voltage/current needed by each unit of the X-ray imaging apparatus 101 from power given by the internal power source 211, and distributes the voltage/current to each unit. While the X-ray imaging apparatus 101 is connected to the power source unit 104, the power source unit 104 supplies power to the power source generation unit 212 via the wired connection unit 210. The power source generation unit 212 can supply power to each unit of the X-ray imaging apparatus 101 using the power supplied from the power source unit 104, and charge the internal power source 211.

The operation unit 207 is used to accept an operation from the user. The implementation method of the operation unit 207 is not particularly limited, and need only be configured to accept an input from the user. More specifically, the operation unit 207 can be implemented by various kinds of switches, a touch panel, and the like to be manually operated by the user. A reception unit for accepting an input from a dedicated remote controller may be provided in the operation unit 207.

The notification unit 208 is used to notify the user or the like of the state of the X-ray imaging apparatus 101 and the like. The notification unit 208 includes a light emitting unit for making a notification by light and a sound-production unit for making a notification by a sound. The implementation method of the notification unit 208 is not particularly limited. The light emitting unit can be implemented by an LED, an LCD monitor, or the like. The sound-production unit is implemented by a loudspeaker, and has a function of implementing various kinds of sound production. The X-ray imaging apparatus 101 according to this embodiment has a notification function (light emitting unit) such as an LED using light and a notification function (sound-production unit) such as loudspeaker using a sound.

Sound-production processing from the notification unit 208 by the X-ray imaging apparatus 101 having the above arrangement will be described with reference to flowcharts shown in FIGS. 3A and 3B.

Upon activation of the X-ray imaging apparatus 101, the control unit 204 is supplied with power and activated. In addition, other function units are supplied with power and activated. Note that at the time of activation of the X-ray imaging apparatus 101, not all the function units of the X-ray imaging apparatus 101 need to be activated. For example, the function units such as the sensor unit 201 used for imaging may not be activated before an imaging request is issued. Such activation control may be implemented by, for example, the control unit 204.

As shown in FIG. 3A, upon activation, the control unit 204 allows an interrupt associated with sound production in step S301. If an interrupt associated with sound production is allowed, interrupt processing shown in FIG. 3B is executed in response to generation of an interrupt signal associated with sound production. The interrupt processing executed when an interrupt signal associated with sound production is generated will be described with reference to the flowchart of FIG. 3B.

When an interrupt signal associated with sound production is generated to start interrupt processing, the control unit 204 determines in step S351 whether the current time falls within a sound-production restricting period. The sound-production restricting period is a period set by the control unit 204 to restrict execution of sound production by the sound-production unit, and will be described in detail later. If it is determined that the current time falls within the sound-production restricting period, the process advances to step S352. In step S352, the control unit 204 suspends a request which has generated the interrupt signal, by holding the request in the storage unit 205, thereby ending the interrupt processing. Note that a request which generates an interrupt is a setting request to set sound production or a sound-production request to execute sound production, as will be described later. In this example, the both requests are suspended. However, only the sound-production request may be suspended.

On the other hand, if it is determined in step S351 that the current time falls outside the sound-production restricting period, the process advances to step S353. In step S353, the control unit 204 determines whether the interrupt has been generated by the sound-production setting request. If it is determined that the interrupt has been generated by the sound-production setting request, the process advances to step S354, otherwise, the process advances to step S356. The sound-production setting request is a request to set ON/OFF of sound production by the sound-production unit, a volume, and the like, and includes setting information about sound production. In steps S354 and S355, the control unit 204 makes settings concerning sound production of the notification unit 208 based on the setting information included in the sound-production setting request.

Note that the setting request concerning sound production is generated in response to a user operation of changing sound-production settings, for example, an operation of turning on/off sound production or an operation of changing the volume. An arrangement for accepting such user operation may be provided in one or both of the operation unit 207 of the X-ray imaging apparatus 101 and the imaging console 102. If, for example, an arrangement for a sound-production setting operation is provided in the operation unit 207 of the main body of the X-ray imaging apparatus 101, an operation input unit such as a switch or dial and a notification unit for notifying the user of an input result by light or a sound are preferably provided in the operation unit 207. It is possible to make sound-production settings and notify the user of a sound-production setting result (whether the current state is a sound-production state, and the degree of volume). Note that the notification unit may be implemented using the notification unit 208.

If a function of performing a sound-production setting operation is provided in the imaging console 102, for example, a method of displaying a setting target item on the display unit, and changing the sound-production settings by operating an instruction input unit such as a keyboard can be adopted. If sound-production settings are made from the imaging console 102, the setting information is transferred to the X-ray imaging apparatus 101 by communication. Based on the received setting information, the control unit 204 of the X-ray imaging apparatus 101 changes the sound-production settings and notifies the user of the setting result using the notification unit (notification unit 208), similarly to a case in which the sound-production settings are changed from the operation unit 207. As described above, in this embodiment, for example, an interrupt for setting sound production is generated when sound-production setting is instructed from the operation unit 207 or sound-production setting is instructed from the sound-production setting screen on the imaging console 102.

Note that a plurality of kinds of notifications using sounds are preferably prepared. This is because the number of states in which the X-ray imaging apparatus 101 makes a notification is larger than one. For example, if the X-ray imaging apparatus 101 is driven by a battery, it is easier to notify the user of the type of problem by differentiating a sound for notifying the user that the remaining battery amount is small from a sound for notifying the user that wireless communication connection is impossible. Therefore, the sound-production unit can prepare a plurality of sounds or melodies by combinations of tones and sound-production times, and produce a sound so that the user can identify each state to be notified. The user can set the correspondence between a state to be notified and the type of sound or melody in the sound-production setting. Furthermore, a volume at the time of sound production can be set for each state to be notified.

If the settings concerning sound production are updated in step S354, the process advances to step S355. In step S355, the control unit 204 notifies the user of the sound-production setting result by causing the notification unit 208 to execute sound production in accordance with the settings updated in step S354. Note that in this embodiment, the sound-production setting result is confirmed after all the settings are made. The present invention, however, is not limited to this. For example, in an arrangement in which each state and a sound indicating each state can be individually set, a sound of a setting result may be confirmed every time the settings are changed. Alternatively, for example, when a sound-production test button provided in the operation unit 207 is operated, sound-production setting confirmation may be executed by interrupt processing. The setting result concerning sound production may be displayed in a visible form on a display unit provided in the notification unit 208 of the X-ray imaging apparatus 101 or the imaging console 102. For example, a method of displaying, by ON/OFF of a specific LED, whether the function of producing a sound is ON or OFF may be used.

On the other hand, if it is determined in step S353 that the interrupt has not been generated by the sound-production setting request, the process advances to step S356. For example, if an event, including a sound-production request, that the remaining amount of the internal power source 211 is insufficient occurs, an interrupt caused by the sound-production request is generated, and the process advances to step S356. Note that the event occurs at an arbitrary timing during the operation of the X-ray imaging apparatus, and examples of the event are detection of the insufficient remaining battery amount and detection of disconnection of communication with the external apparatus. In step S356, the control unit 204 determines whether the interrupt has been caused by the sound-production request to request execution of sound production. If the interrupt has been caused by the sound-production request, the process advances to step S357, and the control unit 204 drives the notification unit 208 to execute sound production in accordance with the sound-production request. In this way, the control unit 204 causes the sound-production unit to execute sound production in response to detection of an event as the source of the sound-production request.

The interrupt processing executed in response to an interrupt signal associated with sound production has been explained. As is well known, the interrupt processing is immediately executed in response to generation of an interrupt signal after an interrupt is allowed in step S301. Therefore, the sound-production settings are updated, as needed, in accordance with a sound-production setting operation, and the loudspeaker of the notification unit 208 produces a sound in response to the occurrence of an event associated with sound production, such as a decrease in battery voltage.

Referring back to FIG. 3A, after allowing an interrupt of the sound-production request in step S301, the control unit 204 determines in step S302 whether an imaging operation request has been issued. An imaging request is issued based on an imaging sequence start instruction from the imaging console 102 or the like.

If it is determined in step S302 that the imaging request has been issued, the process advances to step S303. In steps S303 to S310, X-ray imaging is executed. During X-ray imaging (during a period from imaging preparation to transfer of an X-ray image), the sound-production restricting period during which sound production by the loudspeaker of the notification unit 208 is restricted is set. In this embodiment, the sound-production restricting period includes an image signal readout period by the reading unit 203 from the sensor unit 201. More specifically, the readout period includes a period during which the sample/hold circuit 253 and the multiplexer 254 extract (read out) charges accumulated in the sensor array 251 from a line selected by the drive circuit 252 under the control of the sensor driving unit 202, and a period during which the extracted charges are amplified by the amplifier 255 and digitalized by the A/D converter 256.

Since a readout operation is performed for each line, the time until all of the line set to be read out is set in a readout end state and digitalized corresponds to the readout period. Note that if the X-ray imaging apparatus 101 acquires two images in total, that is, an image for correction and an X-ray image after X-ray irradiation in order to create one image, readout periods for acquiring the respective images are included in the sound-production restricting period. Note that the image for correction is, for example, a dark image (an image acquired from the sensor array without performing X-ray irradiation) representing offset information of the sensor array.

The above-described readout period is a period during which a very small amount of charges necessary for image generation is extracted, and is readily influenced by electromagnetism generated by, for example, driving the coil in the sound-production unit (loudspeaker). Therefore, by setting the readout period as the sound-production restricting period, electromagnetic noise is prevented from generating an induced electromotive force on the sensor array 251 or a current by the induced electromotive force by driving the sound-production unit. Thus, the influence of driving of the sound-production unit on the readout X-ray image can be reduced.

Note that it is possible to suppress the readout period to several sec or less by performing the operations of the sensor driving unit 202 and reading unit 203 at high speed. Therefore, if some sound-production request (interrupt signal) is generated during the readout period, the control unit 204 temporarily, internally suspends the sound-production request, and executes the suspended sound-production request immediately after the end of the sound-production restricting period. The processing will be described below along the flowchart.

In step S303, the control unit 204 performs imaging preparation for X-ray imaging. After completion of the imaging preparation, the control unit 204 starts, in step S304, X-ray imaging in response to an irradiation start request from the X-ray generation console 107, and waits for the end of X-ray imaging (completion of X-ray irradiation). During imaging, charges are accumulated in the respective pixels of the sensor array 251 by emitted X-rays. Upon completion of X-ray irradiation, the control unit 204 starts restricting sound production in step S305, and starts reading out signals from the sensor array 251 by the reading unit 203 in step S306. If the sound production is being performed, the control unit 204 may immediately stop the sound reproduction. This sets the readout period of the X-ray imaging apparatus 101 as the sound-production restricting period. When reading out the image signals, the reading unit 203 causes the amplifier 255 to amplify the image signals read out from the sensor array 251, causes the A/D converter 256 to digitalize the image signals, and stores the digital signals as X-ray image data in the storage unit 205. After that, upon completion of the operation of reading out the image signals from the sensor array 251, the process advances from step S307 to step S308. In step S308, the control unit 204 allows sound production, and ends the sound-production restricting period of the X-ray imaging apparatus 101. If an interrupt signal for requesting sound production is generated during the sound-production restricting period, the sound-production request is suspended by the interrupt processing, as described with reference to FIG. 3B. In step S309, if there is the sound-production request suspended during the sound-production restricting period, the control unit 204 executes sound production by the sound-production unit in accordance with the sound-production request. In step S310, using the communication unit 206, the control unit 204 transfers the X-ray image stored in the storage unit 205 to the imaging console 102.

Note that in the above embodiment, if an interrupt signal is generated during the sound-production restricting period, the sound-production request is suspended by the interrupt processing. The present invention, however, is not limited to this. For example, the interrupt associated with the sound-production request generated during the sound-production restricting period may be suspended, and the control unit 204 may perform, in step S309, sound-production processing associated with the suspended interrupt.

In this embodiment, the interrupt processing is used. However, the present invention is not limited to this. For example, if the occurrence of an event of setting a sound or an event including sound production is detected, a flag indicating it may be held, and confirmed for every predetermined time. If the flag exists, the processing shown in FIG. 3B may be executed. As described above, in an arrangement in which sound-production processing is executed by saving a sound-production request as a flag, and confirming the flag for every predetermined period, a sound-production restricting state can be implemented by, for example, restricting confirmation of the flag during the sound-production restricting period.

An example of the processing when setting the readout period as the sound-production restricting period has been explained. Note that in the above example, the sound-production setting request and the sound-production request are equally restricted during the sound-production restricting period. The present invention, however, is not limited to this. For example, during the sound-production restricting period, the sound-production request may be restricted and the sound-production setting request may be executed. In this case, it is necessary to restrict sound production for confirmation of a setting result. Furthermore, the processing associated with the sound-production settings may be restricted by another timing or a longer period in consideration of actual use. In this case, the control unit 204 sets a setting restricting period for restricting execution of the sound-production setting request in accordance with the operation state of the X-ray imaging apparatus 101, and ignores the setting request generated during the setting restricting period.

Figure 4:
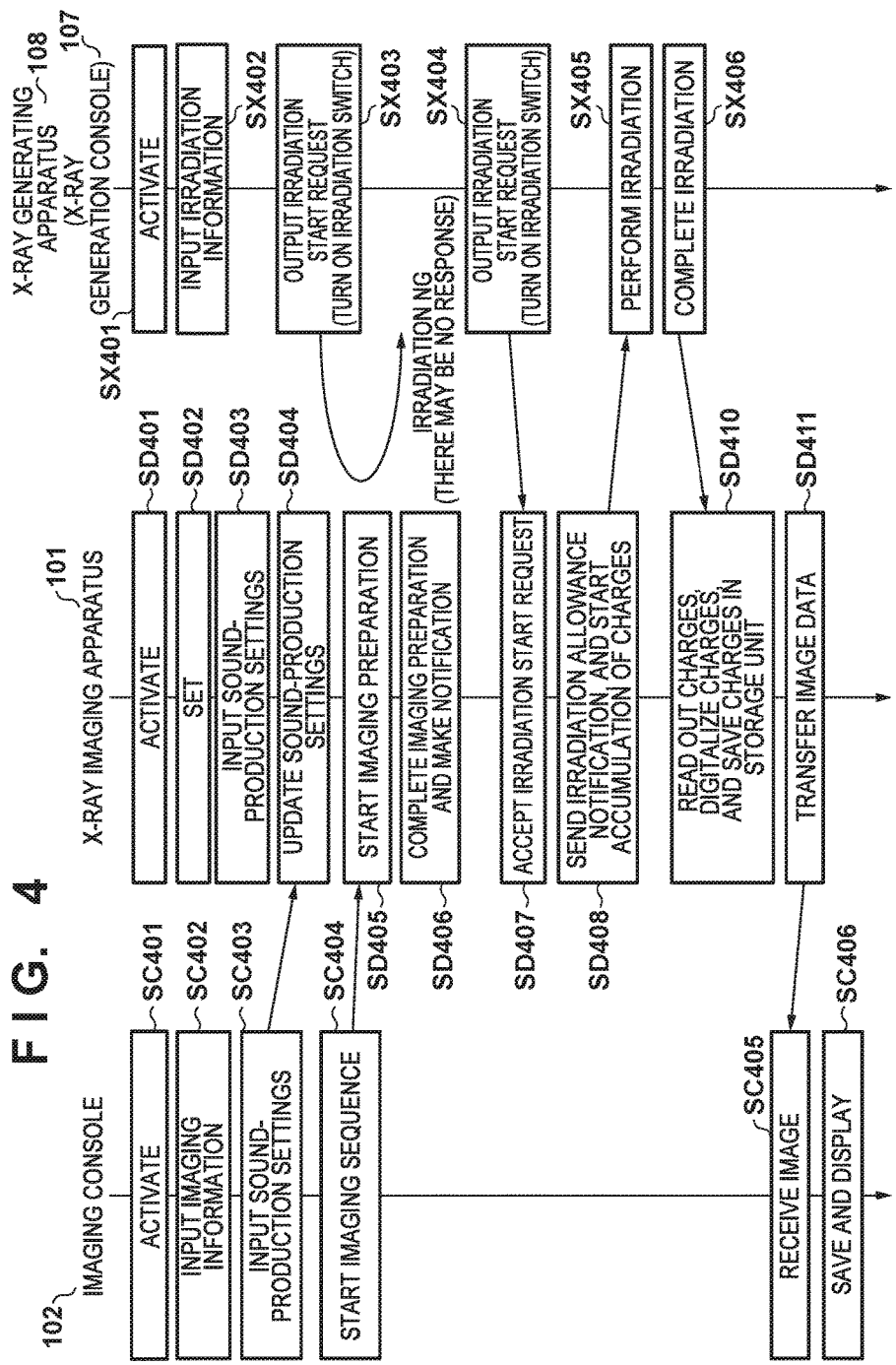
FIG. 4 is a flowchart for explaining the processing relationship between apparatuses at the time of the synchronization mode.

The operation of the X-ray imaging system 100 in the synchronization mode in which the X-ray imaging apparatus 101 executes X-ray imaging in cooperation with the X-ray generating apparatus 108 will be described with reference to a flowchart shown in FIG. 4. FIG. 4 is a flowchart illustrating exchange between the imaging console 102, the X-ray imaging apparatus 101, and the X-ray generating apparatus 108 at the time of imaging according to this embodiment. Note that the X-ray generating apparatus 108 and the X-ray imaging apparatus 101 are connected via the X-ray apparatus connection device 109, as shown in FIG. 1, and are configured to exchange data concerning irradiation allowance. The imaging console 102 and the X-ray imaging apparatus 101 are connected via the LAN 103, as shown in FIG. 1.

To start imaging, the respective apparatuses are activated in steps SC401, SD401, and SX401. In step SC402, the imaging console 102 accepts designation of the X-ray imaging apparatus 101 to be used, and input of imaging information such as an imaging target person and an imaging portion. If the X-ray imaging apparatus 101 to be used is preset at the time of last activation or the like, and it is not necessary to change the setting, designation of the X-ray imaging apparatus can be omitted in some cases. In step SX402, the X-ray generating apparatus 108 accepts irradiation conditions such as the irradiation time and intensity of X-rays input via the X-ray generation console 107.

In addition to the above settings concerning the irradiation conditions and imaging information, the user can make sound-production settings as settings concerning a notification made by the X-ray imaging apparatus 101. Steps SC403 and SD403 indicate that the operation input of the sound-production settings can be accepted. Practical contents of the sound-production settings include the volume of the sound produced from the notification unit 208 (sound-production unit) of the X-ray imaging apparatus 101, and an ON/OFF setting indicating whether to produce a sound, as described above. The sound-production settings can be made from one or both of the imaging console 102 and the operation unit 207 of the X-ray imaging apparatus 101 (steps SC403 and SD403).

If, for example, sound settings are made from the imaging console 102, the imaging console 102 may be configured to make, after setting information of the X-ray imaging apparatus 101 to be used, sound-production settings in the X-ray imaging apparatus 101. Contents of the sound-production settings instructed by the imaging console 102 are sent to the X-ray imaging apparatus 101, and the X-ray imaging apparatus 101 updates the sound-production settings. This is represented by steps SC403 and SD404. If sound settings are made using the operation unit 207 of the X-ray imaging apparatus 101, it is only necessary to change the volume or set whether to output a sound, in accordance with an operation of the switch, the dial, or the like provided in the operation unit 207.

These sound-production settings can be made all the time in principle. However, in consideration of the user's intention to confirm the volume after actually making settings, the sound-production settings can be preferably made while the X-ray imaging apparatus 101 is active. Since it is preferable to be able to confirm a sound immediately after the setting operation by the user, at least a timing before the X-ray imaging apparatus 101 can accept X-ray irradiation to generate an image is preferable. By exemplifying FIG. 4, at a timing before the X-ray imaging apparatus 101 executes step SD405 (imaging preparation start), sound-production settings can be accepted.

When the respective apparatuses of the X-ray imaging system 100 are activated and an imaging sequence can start, an instruction (step SC404) of "imaging sequence start" from the imaging console 102 causes the X-ray imaging apparatus 101 to enter the imaging sequence (step SD405). In this example, the start instruction (imaging sequence start) from the imaging console 102 is used as a trigger.

However, after the respective apparatuses are activated, the X-ray imaging apparatus 101 may transit to an imaging enable state.

Upon receiving an imaging sequence start notification from the imaging console 102, the X-ray imaging apparatus 101 starts preparation in step SD405 so that X-ray irradiation can be performed. More specifically, processing of, for example, supplying a current to the sensor unit 201 and waiting until the operation of a corresponding portion (for example, the sensor array 251) becomes stable is performed. Upon completion of the imaging preparation, the X-ray imaging apparatus 101 can respond to an irradiation request from the X-ray generating apparatus 108, the X-ray generation console 107, or the like. If the X-ray generating apparatus 108 outputs an irradiation start request at a timing (before completion of the imaging preparation) at which the X-ray imaging apparatus 101 cannot allow irradiation (step SX403), the X-ray imaging apparatus 101 outputs an irradiation NG signal or does not respond continuously. If the irradiation NG signal is returned or a non-response state is maintained, the X-ray generating apparatus 108 starts no X-ray irradiation.

Upon completion of the imaging preparation, the X-ray imaging apparatus 101 notifies the user of an irradiation enable state using the notification unit 208 in step SD406. In the notification from the notification unit 208, a notification by light and a notification by a sound are made at the same time. As for a notification by a sound, sound production may be executed only once at the time of completion of the preparation, or a sound may be continuously produced until X-ray irradiation is actually executed. The length of the sound may be changed by the above-described sound-production settings instead of a fixed length. Furthermore, the X-ray imaging apparatus 101 may notify the imaging console 102 of completion of the imaging preparation, and the imaging console 102 may notify the user of completion of the imaging preparation using the display unit.

If the X-ray generating apparatus 108 outputs the irradiation start request, as indicated by step SX404, after the X-ray imaging apparatus 101 enters a state in which it can deal with an irradiation request, the X-ray imaging apparatus 101 returns an irradiation allowance notification to the X-ray generating apparatus 108 in step SD408. The X-ray imaging apparatus 101 causes the sensor array 251 to shift to a state in which charges of an X-ray-charge conversion result are accumulated. Upon receiving the irradiation allowance notification from the X-ray imaging apparatus 101, the X-ray generating apparatus 108 starts X-ray irradiation from the X-ray tube 106 in step SX405. After that, upon completion of X-ray irradiation, the X-ray generating apparatus 108 notifies the X-ray imaging apparatus 101 of it in step SX406.

If the X-ray imaging apparatus 101 receives the irradiation completion notification from the X-ray generating apparatus 108 or a predetermined irradiation time elapses, the X-ray imaging apparatus 101 starts reading out accumulated charges from the sensor array 251 in step SD410. As described above, the X-ray imaging apparatus 101 drives the sensor driving unit 202 and the reading unit 203 to read out the charges (signals) from the sensor array 251, digitalize them, and save the digital signals as image data in the storage unit 205. The signal readout period from the sensor array 251 is set as the sound-production restricting period. During the sound-production restricting period, the X-ray imaging apparatus 101 is in a sound-production restricting state. If a sound-production request is generated during the sound-production restricting period, the sound-production request is suspended, as described above. After the end of the sound-production restricting period, sound production according to the suspended sound-production request is executed.

Examples of the notification contents of the sound-production request which can be generated during the sound-production restricting period are a remaining battery amount warning at the time of battery driving and disconnection of wireless communication when wireless communication is used for communication between the imaging console 102 and the X-ray imaging apparatus 101. For example, if the X-ray imaging apparatus 101 is driven by a battery, the remaining amount of the battery decreases along with the use time, and some functions undesirably stop. Therefore, to prevent functions from suddenly stopping, when the remaining battery amount becomes equal to or smaller than a predetermined amount, the user is notified of it. Therefore, a notification of a decrease in remaining battery amount may coincide with the image readout operation from the sensor array 251. If a notification coincides with the image readout operation from the sensor array 251, driving of the loudspeaker influences the image readout operation. In the above embodiment, as described above, the period including the signal readout period from the sensor array 251 is set as the sound-production restricting period, and a notification is made immediately after the sound-production period. Thus, it is possible to prevent the influence of driving of the sound-production unit as the loudspeaker on the image readout operation.

Note that in the above processing, the sound-production request generated during the sound-production restricting period is suspended, and the suspended sound-production request is executed after the end of the sound-production restricting period. The present invention, however, is not limited to this. For example, the sound-production request generated during the sound-production restricting period may be sent to the external apparatus. For example, if the function of producing a sound is provided in the imaging console 102, the X-ray imaging apparatus 101 may send, to the imaging console 102, the sound-production request accepted during the sound-production restricting period, and the imaging console 102 may perform sound production.

When the image readout operation in step SD410 ends, the X-ray imaging apparatus 101 transfers, in step SD411, the image data stored in the storage unit 205 to the imaging console 102. In step SC405, the imaging console 102 receives the image data sent from the X-ray imaging apparatus 101. In step SC406, the imaging console 102 saves the received image data in a connected storage device (not shown), and displays it on the display unit.

As described above, according to the first embodiment, it is possible to restrict driving of the sound-production component during the image signal readout period from the sensor array 251 associated with image generation, and prevent or reduce the influence of the sound-production component on the X-ray image.

Second Embodiment

The first embodiment has explained the X-ray imaging apparatus which performs an imaging operation in the synchronization mode. The second embodiment will describe an X-ray imaging apparatus which performs an imaging operation in an X-ray irradiation detection mode. An X-ray imaging apparatus 101 according to the second embodiment sets an irradiation detection period in the X-ray irradiation detection mode as a sound-production restricting period in addition to setting of a readout period as a sound-production restricting period.

The X-ray irradiation detection mode and an X-ray irradiation detection function will be described first. The X-ray irradiation detection function is a function of determining the presence/absence of X-ray irradiation by the X-ray imaging apparatus 101 itself, accumulating, if it is determined that X-ray irradiation is being performed, charges by X-rays in a sensor unit 201, and then reading out the charges as an X-ray image. Therefore, exchange of a notification about X-ray irradiation between the X-ray generating apparatus 108 and the X-ray imaging apparatus 101 in the X-ray imaging system 100 according to the first embodiment (FIG. 1) is unnecessary, and the X-ray apparatus connection device 109 and the like can be omitted. The X-ray irradiation detection mode is a mode of acquiring an X-ray image by the above-described X-ray irradiation detection function.

In the X-ray irradiation detection function, an irradiation detection unit 221 shown in FIGS. 2A and 2B is used. As practical implementation methods of the irradiation detection unit 221, there exists a method of detecting X-ray irradiation using the same scintillator and photosensor as those of the sensor unit 201, a method of detecting a current generated in the sensor unit 201 by X-ray irradiation, and the like. As described above, the X-ray irradiation detection function according to this embodiment uses an electrical mechanism (a mechanism using a voltage, a current (charges), or the like is included in part of the X-ray irradiation detection function). Upon detecting X-ray irradiation, the irradiation detection unit 221 notifies a control unit 204 of it. Upon receiving the notification, the control unit 204 starts X-ray imaging using the sensor unit 201. In X-ray imaging, the control unit 204 accumulates charges by X-rays in a sensor array 251 of the sensor unit 201, and controls the sensor unit 201, a sensor driving unit 202, and a reading unit 203 to read out the accumulated charges and generate an X-ray image, as in the synchronization mode.

Figure 5B:
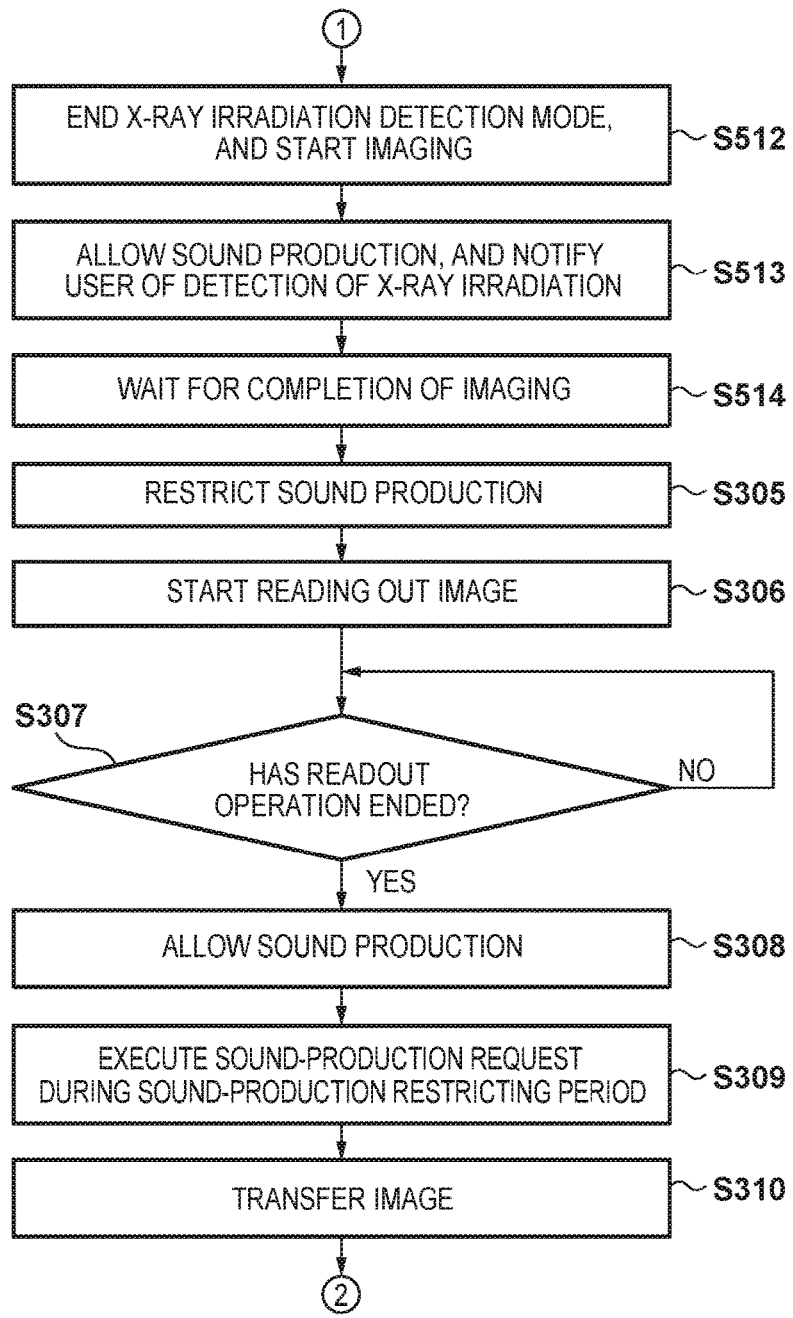

Processing by the X-ray imaging apparatus 101 having the above arrangement according to the second embodiment will be described next with reference to a flowchart shown in FIGS. 5A and 5B. Note that in FIGS. 5A and 5B, the same step numbers as in FIG. 3A denote the same processes. Furthermore, if an event for sound-production settings or an event including sound production occurs, an interrupt caused by a setting request or sound-production request is generated, and interrupt processing shown in FIG. 3B is executed, similarly to the first embodiment.

If the control unit 204 is activated and the interrupt of the sound-production request is allowed (step S301), the process advances to step S501. In step S501, the control unit 204 determines whether a request (a request to shift the X-ray irradiation detection mode) to shift to imaging in the X-ray irradiation detection mode has been issued. If the shift request has been issued, the process advances to step S502. Note that the request to shift to the X-ray irradiation detection mode is given as an imaging sequence start instruction or the like from the imaging console 102 corresponding to the X-ray imaging apparatus 101, as an example. Furthermore, this embodiment assumes imaging in the X-ray irradiation detection mode. However, an arrangement of switching between the X-ray irradiation detection mode and the synchronization mode described in the first embodiment can be adopted. In this case, before step S501, switching between the synchronization mode and the X-ray irradiation detection mode is determined. If the synchronization mode is determined, processes in step S302 and subsequent steps of FIG. 3A are executed. Alternatively, if the X-ray irradiation detection mode is determined, processes in step S501 and subsequent steps are executed.

If sound production is executed during the period (irradiation detection period) when the X-ray irradiation detection function of the irradiation detection unit 221 is operated, a sensitive component such as the irradiation detection unit 221 may be influenced, and the irradiation detection unit 221 may erroneously detect X-ray irradiation and advance an imaging operation. To cope with this, in this embodiment, the irradiation detection period is set as a sound-production restricting period. However, the irradiation detection period may be maintained for a period longer than the sound-production restricting period caused by execution of an image signal readout operation from the sensor array 251. In some irradiation detection methods, as long as a power source can be maintained, the X-ray irradiation detection function is in an enable state, that is, the irradiation detection period is held. Therefore, the possibility that an event including a sound-production request occurs during the irradiation detection period becomes high. It may be impossible to notify the user of a state by a sound because the current time falls within the sound-production restricting period, thereby producing an adverse effect.

Assume, for example, that the X-ray imaging apparatus 101 operates with a battery as an internal power source 211. In this case, if the apparatus shifts to the X-ray irradiation detection mode even though the remaining power of the battery is small, battery may be exhausted during the irradiation detection period. It is desirable to call user's attention before the battery is exhausted. Since, however, the irradiation detection period is set as the sound-production restricting period, sound production for notifying the user of battery exhaustion is unwantedly suspended. As a result, the battery may be exhausted without being noticed by the user.

To prevent such situation, in step S502, based on the current remaining battery amount and the length of the sound-production restricting period caused by the irradiation detection period, the control unit 204 determines whether a sound-production request is generated during the sound-production restricting period. For example, if the upper limit of the irradiation detection period is about 10 minutes, the control unit 204 determines whether the remaining power amount of the internal power source 211 can maintain power supply for 10 minutes. If it is determined that power supply cannot be maintained, it is determined that a sound-production request is generated during the sound-production restricting period. The control unit 204 controls a shift to the X-ray irradiation detection mode based on the determination result. Note that the practical length of the irradiation detection period depends on an X-ray irradiation detection method. If it is determined in step S502 that there is possibility that a sound-production request is generated during the sound-production restricting period caused by the X-ray irradiation detection period, the process advances to step S511.

In step S511, the control unit 204 notifies the user via one or both of a notification unit 208 and an imaging console 102 that an event including sound production occurs during the irradiation detection period or that a shift to the X-ray irradiation detection mode is stopped. The control unit 204 then stops the shift to the X-ray irradiation detection mode. Note that the imaging console 102 also stops the shift to the X-ray irradiation detection mode. After that, the process advances to step S311. If the power is not OFF, the process returns to step S501. If a request to shift to the X-ray irradiation detection mode is generated again, if a factor for determining YES in step S502 is eliminated, the process advances from step S502 to step S503 to execute processing of waiting for detection of X-ray irradiation.

Note that in the above-described processing in step S511, after a notification is made to the user, the shift to the X-ray irradiation detection mode is stopped. The present invention, however, is not limited to this. For example, the user may determine whether the risk can be allowed, and then select to shift to the X-ray irradiation detection mode. In this case, the control unit 204 executes notification to the user in step S511, and then enters a state in which it waits for a user input of determination of whether to forcibly shift to the X-ray irradiation detection mode. If the determination result of the user is input via the operation unit 207 or the imaging console 102, the process shifts to step S503 or S311 in accordance with the determination result.

If it is determined in step S502 that no sound-production request is generated during the irradiation detection period, the process advances to step S503. In step S503, the control unit 204 performs preparation (current supply to necessary functional units, activation of them, or the like) to shift to the X-ray irradiation detection mode. After that, in step S504, the control unit 204 causes the notification unit 208 to notify the user of the start of the X-ray irradiation detection mode by light or a sound. In step S505, the control unit 204 shifts the X-ray imaging apparatus 101 to the X-ray irradiation detection waiting state (irradiation detection period), and restricts sound production according to the sound-production request. Thus, the sound-production restricting period starts.

In step S506, the control unit 204 determines whether the irradiation detection unit 221 has detected X-ray irradiation. If it is determined that X-ray irradiation has been detected, the process advances to step S512; otherwise, the process advances to step S507.

In step S507, the control unit 204 determines whether a predetermined time has elapsed after the start of the X-ray irradiation detection mode, that is, whether a time-out of a detection time occurs. As described above, in some X-ray detection methods, a very long time can be set as an irradiation detection waiting time. However, in consideration of actual use, X-ray detection processing is preferably stopped after a predetermined time as a preparation to a case in which the apparatus is left without X-ray irradiation. Thus, in this embodiment, the time-out of the detection time is set. If the irradiation detection waiting time is limited, it is matter of course that the time-out of the detection time is set. If it is determined in step S507 that the waiting time after the start of the X-ray irradiation detection mode has reached the time-out time, the process advances to step S508 to end the X-ray irradiation detection mode. If it is determined in step S507 that no time-out of the detection time occurs, the process returns to step S506 to determine whether X-ray irradiation has been detected. In the sound-production restricting state, steps S506 and S507 are repeated and the sound-production restricting period continues until a time-out of the detection time occurs or X-ray irradiation is detected.

In step S508, the control unit 204 ends the X-ray irradiation detection mode, and immediately allows sound production. Thus, the sound-production restricting period ends and the sound-production restricting state is canceled. In step S509, the control unit 204 notifies the user of the end of the X-ray irradiation detection mode by a sound or light. Subsequently, in step S510, the control unit 204 executes a sound-production request suspended during the sound-production restricting period (irradiation detection period) if it exists.

If it is determined in step S506 that X-ray irradiation has been detected, in step S512 the control unit 204 ends the X-ray irradiation detection mode and starts imaging (accumulation of charges). In step S513, the control unit 204 allows sound production to end the sound-production restricting period (cancel the sound-production restricting state), and notifies the user of detection of X-ray irradiation. Note that in an arrangement in which the sensor unit 201 used to acquire an X-ray image is also used for detection of X-ray irradiation, in step S512, the same imaging preparation as in the first embodiment (step S303) is executed prior to the start of imaging. In an arrangement in which no sensor unit 201 is used for detection of X-ray irradiation, the sensor unit 201 can be preset in a charge accumulation enable state (imaging preparation completion state). Thus, it is possible to immediately start imaging by skipping imaging preparation after detection of X-ray irradiation.

Subsequently, in step S514, the control unit 204 waits for completion of X-ray imaging (completion of X-ray irradiation). When X-ray irradiation ends, the process advances to step S305 to restrict sound production and read out an image. Processes in steps S305 to S310 are as described in the first embodiment (FIG. 3A). With the above processing, in the second embodiment, the irradiation detection period after shifting to the X-ray irradiation detection mode and the image readout period after imaging are set as sound-production restricting periods, and the influence of the sound-production unit on the irradiation detection operation and the image readout operation can be reduced. If an event including sound production is expected to occur during a scheduled irradiation detection period, a shift to the X-ray irradiation detection mode is stopped. This reduces the adverse effect, on a notification by sound production, of the sound-production restricting period which is caused by the irradiation detection period and can continue relatively long.

The processing of excluding the possibility that a sound-production request is generated in the sound-production restricting state by the processing in step S502 has been explained. An unexpected factor may generate a sound-production request during the sound-production restricting period. In this case, the following processing may be executed.

(1) The sound-production request is suspended until the sound-production restricting period ends (sound production is allowed), and a notification is made after the end of the sound-production restricting period.

(2) A notification is made by light using the light emitting unit provided in the notification unit 208.

(3) Information to be notified is transferred to the external apparatus (for example, the imaging console 102), and a notification is made using the display unit or sound-production mechanism of the imaging console 102. For example, a countdown (time-out countdown) until a time-out of the irradiation detection period occurs is used to make a notification.

(4) If the user is to be notified of serious contents of an error and it is impossible to capture an image in such state, irradiation detection or imaging is stopped, and the sound-production restricting period is terminated (sound production is allowed), thereby executing notification by sound production.

(5) In accordance with the type of event which has occurred, processing is switched to suspend the sound-production request or send the sound-production request to the external apparatus. For example, sound-production requests are ranked in advance, and one of (1) to (4) described above is selected to make a notification in accordance with the rank of the generated sound-production request (that is, the type of event which has occurred). In this case, the event type, the rank of the sound-production request, and processing contents corresponding to the sound-production request are registered in advance. Note that the event type and the processing contents corresponding to the sound-production request may be registered in association with each other without using the rank of the sound-production request.

According to the second embodiment, it is possible to suppress the sound-production component from producing a sound during a period associated with X-ray irradiation detection which is preferably not influenced by the sound-production component, thereby more correctly detecting X-ray irradiation.

Third Embodiment

Each of the first and second embodiments has explained the arrangement in which the imaging console 102 exists in the environment at the timing of imaging. The third embodiment will describe an arrangement in which an X-ray imaging apparatus 101 and an X-ray generating apparatus 108 perform imaging, and there is no imaging console 102 at the timing of imaging. In this specification, a state in which communication with the imaging console 102 is disabled in the environment at the timing of imaging will be referred to as a console-less mode hereinafter. More specifically, the X-ray imaging apparatus 101 is in a mode in which an X-ray image is accumulated in an internal storage unit 205 without being transferred to the imaging console 102 for each imaging operation.

Figures 6A, 6B:
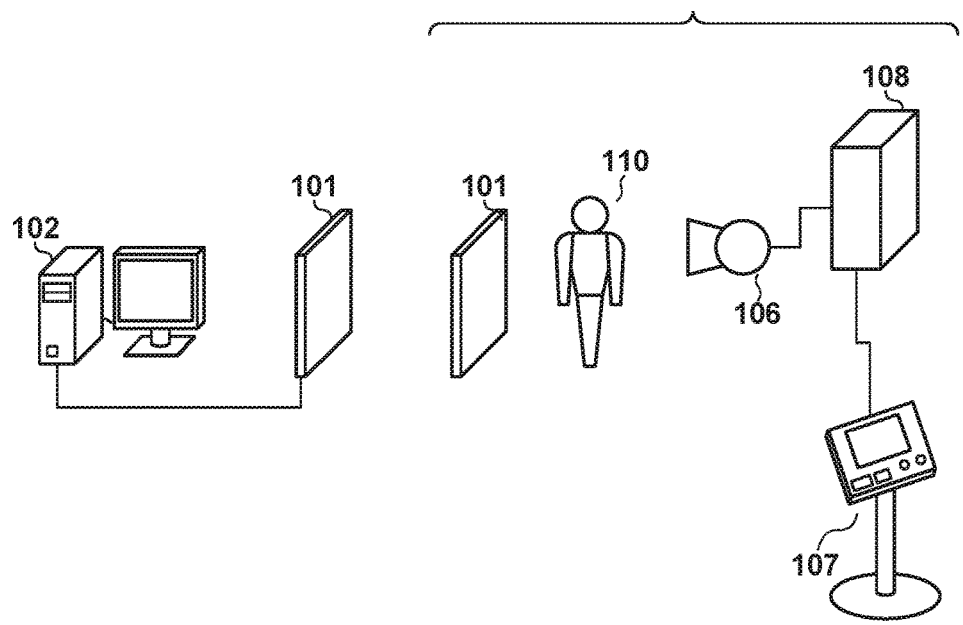
FIGS. 6A and 6B are views showing an example of the arrangement of an X-ray imaging system at the time of a console-less mode.

FIGS. 6A and 6B show an example of the arrangement of an X-ray imaging system according to the third embodiment. An arrangement indicated by FIG. 6A represents an arrangement before or after imaging, and an arrangement indicated by FIG. 6B represents an arrangement during imaging. In the arrangement during imaging (FIG. 6B), the X-ray imaging apparatus 101, the X-ray generating apparatus 108, components (an X-ray tube 106, an X-ray generation console 107, and the like) associated with them, and an object 110 are used to perform imaging, and no imaging console 102 is used. Note that the X-ray generating apparatus 108 is of a standalone type in an imaging room or the like but may be a movable set or an X-ray generating apparatus for round visits which is formed by arranging all the components on a cart.

The arrangements shown in FIGS. 6A and 6B assume an operation in which the X-ray imaging apparatus 101 acquires X-ray images in X-ray imaging, accumulates them in the internal storage unit 205, and collectively outputs the accumulated X-ray images to the imaging console 102 after imaging. To implement such imaging, before imaging, the imaging console 102 and the X-ray imaging apparatus 101 are connected wirelessly or via a cable to set imaging conditions and sound production. After the end of imaging, the X-ray imaging apparatus 101 and the imaging console 102 are connected to transfer X-ray images to the imaging console 102. The arrangement indicated by FIG. 6A shows this state. Note that FIG. 6A shows a state in which the components are connected via a cable but the components may be connected wirelessly. The arrangement of the X-ray imaging apparatus 101 is the same as in the second embodiment. However, the capacity of the storage unit 205 for accumulating captured X-ray images may be made larger.

In the above-described X-ray imaging system according to the third embodiment, the X-ray imaging apparatus 101 and the X-ray generating apparatus 108 cannot be synchronized with each other. Therefore, in the third embodiment, X-ray imaging is executed not in the synchronization mode described in the first embodiment but in the X-ray irradiation detection mode described in the second embodiment. Since no imaging console 102 is connected at the time of X-ray imaging, a requirement to notify the user of state transition by only the X-ray imaging apparatus 101 becomes high. To cope with this, the number of times the X-ray imaging apparatus 101 returns a response to a user operation is increased.

Figure 7B:
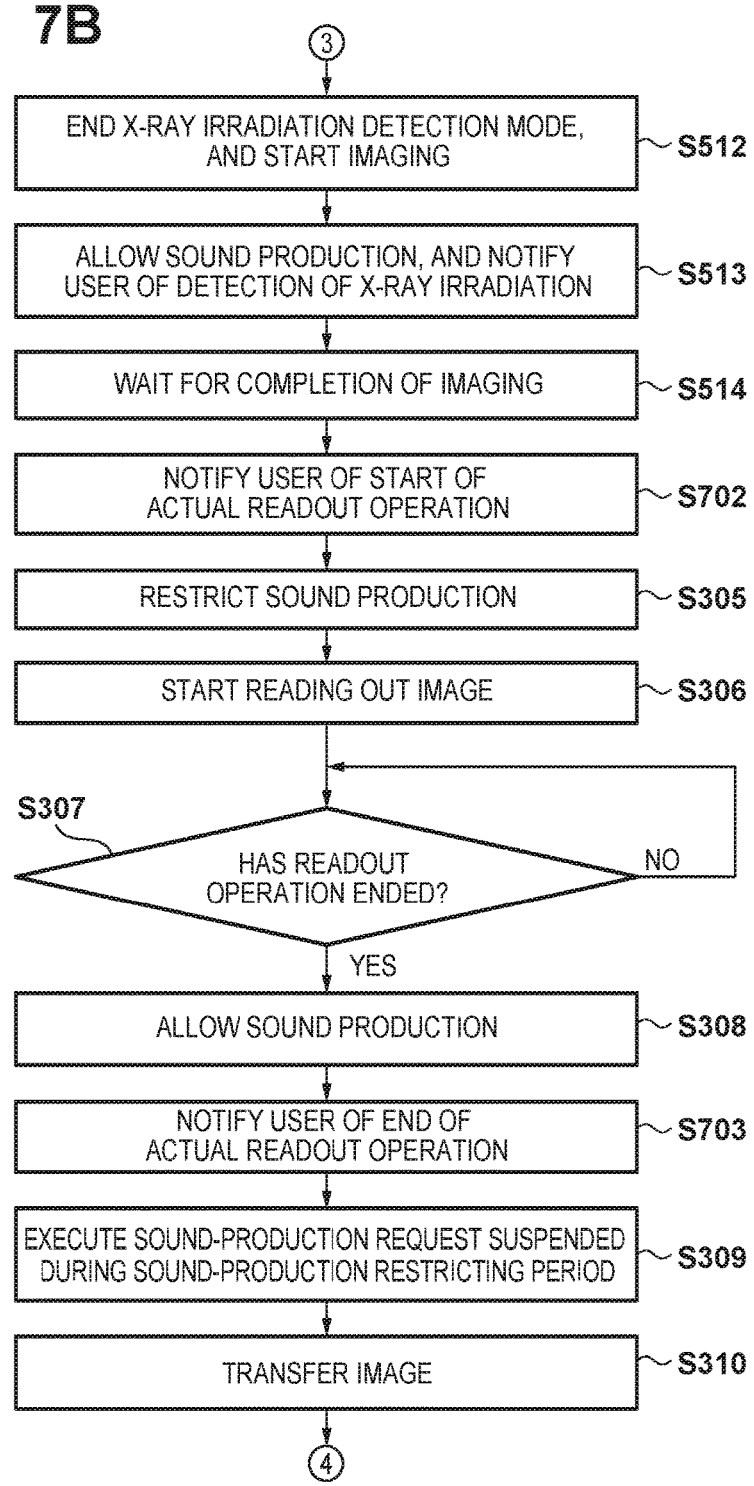

Processing by the X-ray imaging apparatus 101 according to the third embodiment will be described with reference to a flowchart shown in FIGS. 7A and 7B. In FIGS. 7A and 7B, the same reference symbols as in the second embodiment (FIGS. 5A and 5B) denote the same processes. In the first and second embodiments, a setting request concerning sound production from the imaging console 102 can be generated, as needed. To the contrary, in the third embodiment, a period during which a setting request from the imaging console 102 can be sent to the X-ray imaging apparatus 101 corresponds to a period during which the imaging console 102 and the X-ray imaging apparatus 101 are connected before and after X-ray imaging. Generation of a request (setting request or sound-production request) concerning sound production from the X-ray imaging apparatus 101 is the same as in the first and second embodiments.

In the second embodiment, in step S501, the presence of a mode shift request is determined based on an instruction from the imaging console 102. To the contrary, in the third embodiment, an instruction of a mode shift request may be detected in response to a user input to the operation unit 207 or disconnection from the imaging console 102 may be recognized as an instruction of a mode shift request. Furthermore, the operation in the console-less mode described in this embodiment, the operation described in the first embodiment, and the operation described in the second embodiment may be switched. In this case, before execution of step S501, operation switching acceptance processing is performed.

In the third embodiment, step S701 is added after step S511. Similarly to the second embodiment, in step S511, a control unit 204 sends, using the notification unit 208, a notification that a sound-production request can be generated, such as a warning that the remaining battery amount becomes short during the sound-production restricting period, thereby stopping a shift to the X-ray irradiation detection mode. In the console-less mode, there is no advanced user interface such as the imaging console 102 at this time. Therefore, the control unit 204 turns off the power of the X-ray imaging apparatus 101. Note that if the notification unit 208 and an operation unit 207 are advanced and can send a notification of the same information as that of the imaging console 102 or accept it, the same processing as in the second embodiment may be performed.

Processes in steps S702 and S703 are added. In step S702, before the start of the sound-production restricting period, the control unit 204 uses the notification unit 208 to notify the user that the apparatus transits to the sound-production restricting state. In step S703, after the end of the sound-production restricting period, the control unit 204 uses the notification unit 208 to notify the user that the sound-production restricting state is canceled. These notifications are made using one or both of light and a sound. In the console-less mode, there is no imaging console 102 in an imaging environment, and it is thus desirable to increase the opportunity of notifying the user of the state of the X-ray imaging apparatus 101. Therefore, in this embodiment, before and after the sound-production restricting period, the user is notified of the state or operation.

There is a difference from the second embodiment in processing for a sound-production request during the sound-production restricting period. The second embodiment has explained the arrangement of causing the imaging console 102 as an external apparatus to alternatively execute a sound-production request. For example, if it is desirable to notify, by sound production, the user of a time-out countdown during the sound-production restricting period caused by the irradiation detection period, the imaging console 102 is requested to alternatively perform sound production. However, this cannot be performed in the third embodiment. Therefore, in the third embodiment, instead of requesting such external apparatus to alternatively perform sound production, a method of executing sound production with a volume which does not influence the X-ray irradiation detection function, in addition to a notification by the notification unit 208 using light, may be adopted. At this time, settings concerning sound production made by the user are ignored, and a notification is made using a minimum sound.

If notification contents indicate an image acquisition disable state, the control unit 204 may stop X-ray irradiation detection, and end the sound-production restricting period, thereby making a notification using a sound. As described in the above embodiment, a method of setting a notification request level and changing a notification method to a method using only light or a method using light and a sound in accordance with the level is also applicable.

As described above, according to the third embodiment, it is possible to suppress driving of the sound-production component during the irradiation detection period or the readout period during which it is undesirable to receive the influence of driving of the sound-production component, similarly to the second embodiment. In addition, in the third embodiment, while implementing such suppression, it is possible to prevent the opportunity of notifying the user of the state of the X-ray imaging apparatus 101 and its contents from being reduced even in the situation in which there is no imaging console 102.

As described above, the control unit 204 according to each of the above-described embodiments can switch allowance/non-allowance of sound production by the sound-production unit, and sets, as a sound-production restricting period, a period during which the irradiation detection arrangement or the image acquisition arrangement is driven. This prevents the electromagnetism, generated by producing a sound from the sound-production unit, from influencing an irradiation detection operation or an operation of reading out signals from the sensor array.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-023079, filed Feb. 9, 2016, which is hereby incorporated by reference herein in its entirety.

What is claimed is:

1. A radiation imaging apparatus comprising:
a sensor unit including a sensor array configured to generate a signal corresponding to radiation;
a sound-production unit configured to make a notification by sound production;
an internal power source capable of operating the radiation imaging apparatus;
a control unit configured to cause the sound-production unit to execute sound production in response to detection of insufficient remaining amount of the internal power source when the radiation imaging apparatus is operating on the internal power source, wherein
if insufficient remaining amount of the internal power source, which includes a sound-production request, is detected during a first period including a period of reading out a signal from the sensor array, the control unit restricts execution of sound production by the sound-production unit so as to reduce influence caused by execution of the sound-production unit on a signal read from the sensor array during the first period.

2. The apparatus according to claim 1, wherein the first period includes a period of reading out the signal from the sensor array after radiation irradiation to obtain radiation image data.

3. The apparatus according to claim 1, wherein the first period includes a period of reading out the signal from the sensor array to obtain image data for correcting radiation image data.

4. The apparatus according to claim 1, wherein the first period includes a period of digitalizing the signal read out from the sensor array.

5. The apparatus according to claim 1, wherein the first period includes an irradiation detection period for detecting a start of radiation irradiation.

6. The apparatus according to claim 1, wherein the control unit restricts execution of sound production by the sound-production unit during the first period.

7. The apparatus according to claim 1, further comprising:
a suspending unit configured to suspend, when insufficient remaining amount of the internal power source, which includes the sound-production request, is detected during the first period, the sound-production request corresponding to insufficient remaining amount of the internal power source, wherein after an end of the first period, the control unit causes the sound-production unit to execute sound production according to the sound-production request suspended by the suspending unit.

8. The apparatus according to claim 1, wherein when insufficient remaining amount of the internal power source, which includes the sound-production request is detected during the first period, the notification unit sends the sound-production request corresponding to insufficient remaining amount of the internal power to an external apparatus.

9. The apparatus according to claim 1, wherein when insufficient remaining amount of the internal power source, which includes the sound-production request, is detected during the first period, the notification unit makes a notification representing occurrence of insufficient remaining amount of the internal power source using an arrangement different from sound production by the sound-production unit.

10. The apparatus according to claim 1, wherein when image acquisition by the radiation imaging apparatus becomes impossible, the control unit causes the sound-production unit to execute sound production corresponding to insufficient remaining amount of the internal power source regardless of the first period.

11. The apparatus according to claim 1, wherein before or after the first period, a notification representing a state of the radiation imaging apparatus is made.

12. The apparatus according to claim 1, further comprising:
a changing unit configured to change a sound-production setting in the sound-production unit in accordance with a sound-production setting request, wherein
the changing unit ignores the setting request generated during the first period.

13. The apparatus according to claim 1, further comprising:
a changing unit configured to change a sound-production setting in the sound-production unit in accordance with a sound-production setting request, wherein
the changing unit sets a second period in accordance with an operation state of the radiation imaging apparatus, and
the changing unit ignores the setting request generated during the second period.

14. The apparatus according to claim 1, wherein the control unit causes the sound production unit to execute sound production in response to detection of an event associated with a countdown until a time-out of the irradiation detection period for detecting the start of radiation irradiation occurs.

15. The apparatus according to claim 1, wherein the control unit detects insufficient remaining amount of the internal power source when remaining amount of the internal power source becomes equal to or smaller than a predetermined amount.

16. The apparatus according to claim 1, wherein the sensor unit and the sound-production unit are accommodated in one housing.

17. A control method for a radiation imaging apparatus including a sensor unit with a sensor array configured to generate a signal corresponding to radiation; a sound-production unit configured to make a notification by sound production; and an internal power source wherein the radiation imaging apparatus is operable by the internal power source, the method comprising:
causing the sound-production unit to execute sound production in response to detection of insufficient remaining amount of the internal power source when the radiation imaging apparatus is operating on the internal power source; and
restricting, if insufficient remaining amount of the internal power source, which includes a sound-production request, is detected during a first period including a period of reading out a signal from the sensor array, execution of sound production by the sound-production unit so as to reduce influence caused by execution of the sound-production unit on a signal read from the sensor array during the first period.

18. A non-transitory computer-readable storage medium that stores a program for causing a computer to execute a control method for a radiation imaging apparatus including a sensor unit with a sensor array configured to generate a signal corresponding to radiation; a sound-production unit configured to make a notification by sound production; and an internal power source wherein the radiation imaging apparatus is operable by the internal power source, the method comprising:
causing the sound-production unit to execute sound production in response to detection of insufficient remaining amount of the internal power source when the radiation imaging apparatus is operating on the internal power source; and
restricting, if insufficient remaining amount of the internal power source, which includes a sound-production request, is detected during a first period including a period of reading out a signal from the sensor array, execution of sound production by the sound-production unit so as to reduce influence caused by execution of the sound-production unit on a signal read from the sensor array during the first period.

* * * * *